United States Patent [19]
Syed et al.

[11] Patent Number: 5,641,477
[45] Date of Patent: *Jun. 24, 1997

[54] REDUCTION OF HAIR DAMAGE DURING LANTHIONIZATION WITH HAIR RELAXERS CONTAINING DESWELLING AGENTS

[75] Inventors: Ali N. Syed, Orland Park; Kaleem Ahmad, Chicago, both of Ill.

[73] Assignee: Avlon Industries, Inc., Bedford Park, Ill.

[*] Notice: The term of this patent shall not extend beyond the expiration date of Pat. No. 5,348,737.

[21] Appl. No.: 345,587

[22] Filed: Nov. 28, 1994

[51] Int. Cl.$^6$ ................................ A61K 7/09; A61K 7/06
[52] U.S. Cl. ...................... 424/70.4; 424/70.2; 132/204
[58] Field of Search ........................ 424/424, 70.4, 424/205, 70.2; 132/204

[56] References Cited

U.S. PATENT DOCUMENTS

| | | | |
|---|---|---|---|
| 4,303,085 | 12/1981 | de la Guardia et al. | 132/7 |
| 4,313,933 | 2/1982 | Yamazaki | 424/22 |
| 4,314,572 | 2/1982 | de la Guardia et al. | 132/7 |
| 4,371,517 | 2/1983 | Vanlerberghe et al. | 424/70 |
| 4,579,131 | 4/1986 | Syed | 132/7 |
| 4,605,018 | 8/1986 | de la Guardia et al. | 132/7 |
| 4,871,530 | 10/1989 | Grollier et al. | 424/47 |
| 4,913,900 | 4/1990 | Kolc et al. | 424/72 |
| 4,947,878 | 8/1990 | Crews et al. | 132/203 |
| 5,057,311 | 10/1991 | Kamegai et al. | 424/70 |
| 5,060,680 | 10/1991 | Akhtar | 132/204 |
| 5,294,438 | 3/1994 | Chang | 424/73 |
| 5,340,570 | 8/1994 | Wong | 424/71 |
| 5,348,737 | 9/1994 | Syed et al. | 424/70.1 |

OTHER PUBLICATIONS

Yoshiko et al., JAPID abstract of JP4198119, 1992.
Hiroatsu, JAPIO abstract of JP55 149206, 1980.
C.E. Orfanos, W. Montagna and G. Stuttgen; Hair Research Status and Future Aspect; Springer–Verlag Berlin Heidelberg New York 1981; pp. 116–121.
Ali N. Syed; Ethnic Hair Care: History, Trends and Formulation; Cosmetics & Toiletries, Allure Publishing Corp. 1993; pp. 99–107.
Charles Zviak; Permanent Waving and Hair Straightening; L'Oreal, Paris, France; The Science of Hair Care Care; Marcel–Dekker, Inc., New York, N.Y.; 1986.
E. Tolgyesi and F. Frang; Action of Nucleophilic Reagents on Hair Keratin; Gillette Research Institute, Rockville, MD, USA; Spring–Verlag Berlin Heidelberg 1981; pp. 116–122.
G. Stuttgen; Introduction: Human Hair and Scalp in View of the Use of Hair Care Products; Dept. of Dermatology at the Rudolph–Virchow–Hospital, The Free University Berlin, Berlin, Germany; Springer–verlag Berlin Heidelberg 1981; pp. 477–500.

*Primary Examiner*—Sallie M. Gardner
*Attorney, Agent, or Firm*—Gardner, Carton & Douglas

[57] ABSTRACT

This invention relates to a process for relaxing hair fibers that comprises applying to the hair fibers a lanthionizing composition that comprises a hydrogenated starch hydrolysate and/or a sugar. The present invention also provides a lanthionizing composition that comprises hydrogenated starch hydrolysate and/or a sugar which decreases the amount of damage that occurs to hair fibers during the lanthionization process.

18 Claims, No Drawings

REDUCTION OF HAIR DAMAGE DURING LANTHIONIZATION WITH HAIR RELAXERS CONTAINING DESWELLING AGENTS

TECHNICAL FIELD

This invention relates to a process for relaxing hair fibers. This invention also relates to a chemical composition for relaxing hair fibers.

BACKGROUND OF THE INVENTION

Human hair has a variety of textures, from fine to coarse, and from straight to curly. The ability to alter or change the texture of hair through chemical processes is important both for men and women, and hair care products and chemical processes that can alter the texture of hair are in great demand. For example, individuals with excessively curly hair seek products that can straighten or "relax" hair.

The relaxing process operates by changing the chemical structure of hair fibers. Hair fibers are comprised of keratin, which is in turn comprised of polypeptide chains bonded together by three types of bonds: cystine (or disulfide) bonds, hydrogen bonds and salt linkages. The relaxing process operates primarily on the cystine bonds. When the cystine bonds are exposed to an alkaline relaxing solution, they are transformed to lanthionine bonds. The chemical term for the hair relaxation process is lanthionization.

In a typical relaxation process, an alkaline relaxing cream is applied to the hair for a time period sufficient to obtain the desired degree of relaxation, typically about 18–20 minutes. During this step, hair visually becomes physically straighter. After the alkaline relaxing cream has been left on the hair for the desired time, it is usually rinsed from the hair with water.

Although the conventional relaxation process decreases the amount of curl in hair, it also damages the hair. The conventional relaxation process causes hair fibers to longitudinally split and break, leaving hair coarse, brittle and unmanageable, which is described in U.S. Pat. No. 5,348,737, which is hereby incorporated by reference. These results cannot be corrected by applying conditioning agents to the hair subsequent to the relaxation process. Therefore, individuals wishing to straighten their hair using the conventional relaxation process must suffer the damaging structural effects of the process on their hair.

It is also known that hair fibers swell in the presence of water, and that excessive swelling can also result in structural damage to hair fibers. Swelling occurs in both the hair fiber cortex and the hair fiber cuticle, the respective inner and outer portions of the hair fiber. Structural damage to the fiber occurs when the cortex continues to swell after the cuticle has ceased swelling causing the cuticle to rupture, thereby rendering the hair damaged, dull and difficult to manage. Moreover, the damage done to the hair during relaxation can result in a decrease in the tensile strength of the hair which can cause difficulties when combing the hair while it is either wet or dry.

In general, hair relaxers can be purchased in the form of creams which contain active ingredients such as sodium hydroxide (lye) or guanidine hydroxide. (Compositions that contain guanidine hydroxide have been called "No Lye" relaxers.) Both lye containing relaxers and relaxers that do not contain lye, when applied to hair, decrease the tensile strength of hair considerably. For example, the hair fibers can lose as much as 45–55% of their tensile strength when the hair fibers are wet.

The present invention provides a process for relaxing hair fibers in which swelling is minimized and damage to the resulting hair fibers is also significantly decreased. Also provided is a composition for relaxing hair fibers which provides for decreased hair fiber swelling and decreased damage of the hair fibers.

SUMMARY OF THE INVENTION

A process for relaxing hair fibers is disclosed. The process comprises the steps of applying to the hair fibers a lanthionizing composition that comprises a hydrogenated starch hydrolysate and/or a sugar; allowing the lanthionizing composition to remain on the hair fibers for a time sufficient to obtain the desired degree of lanthionization; and removing the lanthionizing composition from the hair fibers. Also provided is a lanthionizing composition that comprises a hydrogenated starch hydrolysate and/or a sugar.

DETAILED DESCRIPTION OF THE PREFERRED EMBODIMENTS

The present invention provides a process for relaxing hair fibers. The process comprises applying to hair fibers a lanthionizing composition that comprises a hydrogenated starch hydrolysate and/or a sugar; allowing the lanthionizing composition to remain on the hair fibers for a time sufficient to obtain the desired degree of lanthionization; and removing the lanthionizing composition from the hair fibers.

It is contemplated that those lanthionizing compositions that are known in the art can be used in the present invention. A typical lanthionization composition contains, as the active ingredient, about 2.4% by weight of the composition of a nonreducing base such as sodium hydroxide (lye) or guanidine hydroxide, and lanthionization compositions generally have a pH in the range of about 12.0 to about 13.5 One suitable lanthionization composition is AFFIRM® Cream Relaxer available from Avlon Industries, Chicago, Ill.

It is also contemplated that the lanthionizing composition can be a multi-part or single-part system. In a multi-part system, the parts are combined to form the lanthionizing composition. For example, multi-part lanthionizing compositions having two parts are known, and the active ingredient, e.g., guanidine hydroxide, is generated in situ by the combination of the two parts. Typically, a multi-part lanthionization composition includes a cream relaxer as a first part and a liquid activator as a second part. When the first and second parts are mixed together, the active hair relaxing ingredient is formed.

In the present invention, lanthionizing compositions known in the art are modified by adding a hydrogenated starch hydrolysate and/or a sugar. The addition of a hydrogenated starch hydrolysate and/or a sugar directly to the lanthionization composition, surprisingly, results in hair that has a greater tensile strength and has been less damaged than when a lanthionization composition that does not contain a hydrogenated starch hydrolysate and/or a sugar is used to relax hair. It is contemplated that a lanthionization composition may contain one or more hydrogenated starch hydrolysates, or one or more sugars, or a combination of hydrogenated starch hydrolysates and sugars.

The hydrogenated starch hydrolysate and/or sugar may be found in the composition in the range of about 0.1% to about 5.0% by weight of the entire lanthionizing composition. Preferably, the hydrogenated starch hydrolysate and/or sugar is found in the composition in the range of about 0.25% to about 3.0%, and most preferably, the hydrogenated starch hydrolysate and/or sugar is found in the composition in the range of about 1.0% to about 1.5%.

Representative examples of hydrogenated starch hydrolysate include, but are not limited to, Hystar 6075, Hystar HM 75 and Hystar 7000, all of which may be obtained from Lonza, Inc., Fairlawn, N.J.

Representative sugars that can be used in the present invention include, but are not limited to, sucrose, glucose, fructose, sorbitol and glycerol. Preferably, however, the sugar is sucrose or sorbitol (Hystar CG).

The lanthionizing composition of the present invention is applied to the hair to be relaxed. The composition may be in the form of a solution, or preferably, the lanthionizing composition is in the form of a cream.

The lanthionizing composition is allowed to remain on the hair fibers for a time sufficient to obtain the desired degree of lanthionization. During this time, the hair fibers may be pressed, flattened or combed. Because there are many different types of hair, the amount of time that the lanthionizing composition may be left on the hair will depend on the type of hair and the desired degree of straightness or relaxation. In general, the longer the lanthionizing composition is left on the hair fibers, the straighter the hair fibers become. However, it is undesirable to leave the lanthionizing composition on the hair fibers too long, as damage to the hair fibers results. Those skilled in the art are familiar with the times necessary to achieve the desired degree of straightness for different types of hair. Moreover, those skilled in the art are also able to monitor the progress of the lanthionization process to obtain the desired degree of straightness.

Next, the lanthionizing composition is removed from the hair fibers. Typically, this is done by washing the lanthionizing composition from the hair fibers using water. However, any method known to those skilled in the art for removing a lanthionizing composition from hair fibers can be used.

The application of compositions to hair fibers subsequent to the relaxation process is known to those skilled in the art. For example, the application of conditioners to soften the hair fibers after lanthionization is well known.

While not wishing to be bound by theory, it is believed that the addition of a hydrogenated starch hydrolysate and/or a sugar to a lanthionizing composition helps decrease the swelling of the hair when the lanthionizing composition is applied, and thus, acts as a de-swelling agent.

It is believed that the deswelling agents of the present invention decrease the swelling of the hair fiber by reducing the osmotic pressure in the hair fiber; that is, not letting the osmotic pressure build to any considerable degree. During the lanthionization process, the nonreducing base of the lanthionization composition penetrates the hair fiber. The hair fiber can act like a semi-permeable membrane, osmotic pressure generally builds up within the hair fiber, and water flows into the hair fiber. Because of deswelling agents present in lanthionization cream, the degree of swelling during lanthionization is minimized, hence causing less damage to hair fibers.

In one embodiment of the invention, the lanthionizing composition and the deswelling agents are combined in one container. In another embodiment of the invention, the lanthionizing composition and the deswelling agents are contained in separate containers, which are combined prior to application of the lanthionization composition to the hair fibers. In any event, the lanthionizing composition and the deswelling agents are mixed and applied to the hair fibers at once.

The following examples are intended to be illustrative of specific embodiments of the invention. These examples are not intended to limit the specification or the claims in any manner.

EXAMPLES

Lanthionizing Compositions

Tables A and B below show examples of lanthionizing compositions having sodium hydroxide or guanidine hydroxide as the nonreducing base. Included in some compositions are a hydrogenated starch hydrolysate and/or a sugar.

TABLE A

SODIUM HYDROXIDE LANTHIONIZING COMPOSITIONS
% By Weight

| INGREDIENTS | A | B | C | D | E | F |
|---|---|---|---|---|---|---|
| Deionized Water | 52.15 | 50.65 | 50.75 | 50.75 | 50.65 | 51.10 |
| Sodium Hydroxide | 4.35 | 4.35 | 4.35 | 4.35 | 4.35 | 4.35 |
| PEG-50 Lanolin | 0.50 | 0.50 | 0.50 | 0.50 | 0.50 | 0.50 |
| Hystar CG | — | 1.50 | — | — | — | — |
| Hystar 6075 | — | — | 1.40 | — | — | — |
| Hystar 7000 | — | — | — | — | 1.50 | — |
| Hystar HM 75 | — | — | — | 1.40 | — | — |
| Sucrose | — | — | — | — | — | 1.05 |
| Petrolatum | 12.00 | 12.00 | 12.00 | 12.00 | 12.00 | 12.00 |
| Mineral Oil | 18.00 | 18.00 | 18.00 | 18.00 | 18.00 | 18.00 |
| Laneth-15 | 1.00 | 1.00 | 1.00 | 1.00 | 1.00 | 1.00 |
| Emulsifying Wax | 11.00 | 11.00 | 11.00 | 11.00 | 11.00 | 11.00 |
| Cetyl Alcohol | 1.00 | 1.00 | 1.00 | 1.00 | 1.00 | 1.00 |

TABLE B

GUANIDINE HYDROXIDE LANTHIONIZING COMPOSITIONS
% By Weight

PART A: CREAM

| INGREDIENTS | A | B | C | D | E | F |
|---|---|---|---|---|---|---|
| Deionized Water | 52.73 | 51.23 | 49.08 | 48.98 | 49.08 | 49.44 |
| Calcium Hydroxide | 5.50 | 5.50 | 5.50 | 5.50 | 5.50 | 5.50 |
| PEG-50 Lanolin | 2.25 | 2.25 | 2.25 | 2.25 | 2.25 | 2.25 |
| Hystar CG | — | 1.50 | — | — | — | — |
| Hystar 6075 | — | — | 1.40 | — | — | — |
| Hystar 7000 | — | — | — | 1.50 | — | — |
| Hystar HM 75 | — | — | — | — | 1.40 | — |
| Sucrose | — | — | — | — | — | 1.05 |
| Petrolatum | 12.00 | 12.00 | 12.00 | 12.00 | 12.00 | 12.00 |
| Mineral Oil | 18.00 | 18.00 | 18.00 | 18.00 | 18.00 | 18.00 |
| Fatty Alcohol | 8.00 | 8.00 | 8.00 | 8.00 | 8.00 | 8.00 |
| Ceteth-20 | 1.50 | 1.50 | 1.50 | 1.50 | 1.50 | 1.50 |
| Mazu DF 200S | 0.02 | 0.02 | 0.02 | 0.02 | 0.02 | 0.02 |

PART B: LIQUID ACTIVATOR

| INGREDIENTS | % BY WEIGHT |
|---|---|
| Guanidine Carbonate | 27.2000 |
| Deionized Water | 72.5994 |
| Versene 220 | 0.2000 |
| FD & C Red #40 | 0.0006 |

Mazu DF 200S may be obtained from Mazer Chemicals, Inc., in Gurnee, Illinois, and Versene 220 may be obtained from Van Waters & Rogers, Inc. of Chicago Heights, Illinois.

Tensile Strength of Hair Fibers—General Protocol i) Twelve inch long, European dark brown hair was obtained from DeMeo Brothers, New York. Hair fibers were washed with a mild shampoo containing 10% ammonium lauryl sulfate. The fibers were rinsed with tepid tap water for two minutes and dried overnight at an ambient temperature.

ii) The cleansed fibers of close diameters (71–80 microns) were selected for this study. Each fiber was crimped into two 30 mm sections. The sections toward the root end were identified as Group A and were numbered as Fibers 1 through 25. The sections towards the middle of the fiber were designated as Group B and were numbered as Fibers 26 through 50.

iii) Group A and Group B Fibers were immersed in water at 21° C. for at least 30 minutes before determining the work required to extend them 20% of their original length of 30.0 min.

iv) The work required for 20.0% elongation was done with the fibers immersed in water at controlled temperature of 21 ° C. by using Dia-Stron Miniature Tensile Test manufactured by Dia-Stron Limited of the United Kingdom at the following parameters:

| | |
|---|---|
| Range | 50.0 gms. |
| Gauge | 2.0 gms. |
| Sample Size | 30.0 mm |
| Phase 1 | 20.0% |
| Phase 2 | 0.0 sec. |
| Phase 3 | 0.0% |
| Phase 4 | 0.0 sec. |
| Speed | 10.0 mm/min. |
| No. of Cycles | 1 Cycle |

The initial work done for untreated fibers was equal to X.

v) The fibers of each group were then immersed in water and allowed to recover overnight.

vi) Group A and Group B fibers were mounted on separate rectangular processing slabs and allowed to dry to room temperature for 30 minutes before relaxer treatment.

vii) Group A fibers were treated with composition A shown in Table A or B, and Group B were treated with a different composition from Table A or B for 18 minutes. The groups were rinsed with tepid tap water for 3 minutes and treated with diluted non-conditioning normalizing shampoo for 3 minutes separately. They were then rinsed with tepid water for 1 minute, unmounted and stored overnight in water without allowing the fibers to dry.

viii) The Group A and Group B fibers were then elongated 20.0% as above using a Dia-Stron Miniature Tensile Test while fibers were still kept immersed in water. The work done on the treated fibers after relaxer treatment was equal to Y.

ix) The F20 index for each group of fibers was determined according to the following formula:

F20 Index = Loss in Tensile Strength at 20.0% Extension $$F20 = \frac{X-Y}{X} \times 100$$

The following examples (1–10) show the results of the tensile strength test for various lanthionizing compositions.

Example 1

Group A Fibers were treated with sodium hydroxide relaxer without Hystar CG (Composition A of Table A) and Group B Fibers were treated with sodium hydroxide relaxer containing 1.5% Hystar CG (Composition B of Table A). The results are shown in Tables 1 and 2.

TABLE 1

GROUP A WET FIBERS: CONTROL TREATED WITH SODIUM HYDROXIDE RELAXER WITHOUT HYSTAR CG

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 2 | 1.610 | 0.751 | 53.35 |
| 6 | 1.490 | 0.734 | 50.74 |
| 7 | 1.060 | 0.518 | 51.13 |
| 8 | 1.340 | 0.571 | 57.39 |
| 9 | 0.993 | 0.432 | 56.50 |
| 10 | 1.310 | 0.628 | 52.06 |
| 12 | 1.540 | 0.698 | 54.68 |
| 14 | 1.260 | 0.538 | 57.30 |
| 18 | 1.250 | 0.578 | 53.76 |
| 19 | 1.090 | 0.534 | 51.01 |
| 20 | 0.980 | 0.457 | 53.37 |
| 21 | 0.973 | 0.462 | 52.52 |
| 22 | 1.530 | 0.775 | 49.35 |
| 24 | 1.240 | 0.606 | 51.13 |
| 25 | 1.230 | 0.602 | 51.06 |
| AVERAGE | | | 53.02 |
| STANDARD DEVIATION (SAMPLES) | | | 2.51 |
| COEFFICIENT OF VARIANCE | | | 4.73 |

*WORK DONE IN MILLIJOULES

TABLE 2

GROUP B WET FIBERS: EXPERIMENTAL TREATED WITH SODIUM HYDROXIDE RELAXER WITH 1.5% HYSTAR CG

| | INITIAL WORK DONE* X | WORK DONE* AFTER RELAXER Y | F20 INDEX AFTER RELAXER TREATMENT (% Loss in Tensile Strength) |
|---|---|---|---|
| 27 | 1.660 | 0.862 | 48.07 |
| 31 | 1.360 | 0.636 | 49.56 |
| 32 | 1.060 | 0.526 | 50.36 |
| 33 | 1.270 | 0.633 | 50.16 |
| 34 | 0.849 | 0.440 | 48.17 |
| 35 | 1.170 | 0.651 | 44.36 |
| 37 | 1.290 | 0.721 | 44.11 |
| 39 | 1.320 | 0.632 | 52.12 |
| 43 | 1.140 | 0.589 | 48.33 |
| 44 | 1.060 | 0.579 | 46.39 |
| 45 | 0.895 | 0.420 | 53.07 |
| 46 | 0.967 | 0.516 | 46.64 |
| 47 | 1.300 | 0.649 | 50.08 |
| 49 | 1.380 | 0.717 | 48.04 |
| 50 | 1.070 | 0.579 | 45.89 |
| AVERAGE | | | 48.36 |
| STANDARD DEVIATION (SAMPLES) | | | 2.61 |
| COEFFICENT OF VARIANCE | | | 5.40 |

*WORK DONE IN MILLIJOULES

Table 1 and 2 show that Group A fibers have avenge F20 Index loss of 53.02% and Group B fibers have an avenge F20 Index loss of 48.36%. The t-value equals 3.91. The t-value from Student-t table at 14 degrees of freedom and 95% probability is equal to 2.145. Therefore, Group B wet fibers which are treated with sodium hydroxide relaxer containing 1.5% Hystar CG show significantly less decrease in the tensile strength at 20.0% elongation than Group A wet fibers treated with sodium hydroxide relaxer without Hystar CG.

Statistical Analysis

Shown below is an example of the statistical analysis performed on the data of Example 1 (Tables 1 and 2). The Student t-Test is well known.

Student $t$-Test $$t = \frac{\bar{X}_1 - \bar{X}_2}{Sd} \times \sqrt{\frac{N_1 \times N_2}{N_1 + N_2}}$$

Where . . .

$X_1$=Mean or Average of F20 Index in Table 1
$X_2$=Mean or Average of F20 Index in Table 2
$N_1$=No. of Readings in Table 1
$N_2$=No. of Readings in Table 2

Whereas $$Sd = \sqrt{Sd^2}$$

And . . .

$$Sd^2 = \frac{S_1^2(N_1-1) + S_2^2(N_2-1)}{N_1 + N_2 - 2}$$

Where $S_1$=Standard Deviation of Group A F20 Index
$S_2$=Standard Deviation of Group B F20 Index Compare the value of t-calculated as above, against the t-value from a Student-t table, which are known to those skilled in the art.

Comparison of Average F20 Index of Group A and Group B Fibers for Example 1

$S_1 = 2.51$ from Table 1
$S_2 = 2.61$ from Table 2
$N_1 = 15$
$N_2 = 15$ $$Sd = \sqrt{Sd^2} = \sqrt{\frac{S_1^2(N_1-1) + S_2^2(N_2-1)}{N_1 + N_2 - 2}}$$

$$= \sqrt{\frac{(2.51)^2(15-1) + (2.61)^2(15-1)}{15+15-2}}$$

$$= 2.56$$

$$t = \frac{\bar{X}_1 - \bar{X}_2}{Sd} \times \sqrt{\frac{N_1 \times N_2}{N_1 + N_2}}$$

$$= \frac{53.02 - 48.36}{2.56} \times \sqrt{\frac{15 \times 15}{15+15}}$$

$$= 3.91$$

When $\bar{X}_1 = 53.02$ . . . Table 1

$\bar{X}_2 = 48.36$ . . . Table 2

The t-value from the Student-t table at 95.0% probability and 14 degrees of freedom is 2.145, which is less than t-value calculated for this experiment. Therefore, Group B fibers are significantly less damaged at 95.0% probability.

A similar analysis was carried out for Examples 2–10.

Example 2

Group A fibers were treated with sodium hydroxide relaxer without Hystar 6075 (Composition A of Table A) and Group B fibers were treated with sodium hydroxide relaxer containing 1.4% Hystar 6075 (Composition C of Table A). The results are shown in Tables 3 and 4.

TABLE 3

GROUP A WET FIBERS: CONTROL TREATED WITH SODIUM HYDROXIDE RELAXER WITHOUT HYSTAR 6075

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 0.900 | 0.381 | 57.67 |
| 2 | 0.800 | 0.342 | 57.25 |
| 3 | 1.380 | 0.739 | 46.45 |
| 4 | 1.270 | 0.548 | 56.85 |
| 7 | 1.120 | 0.476 | 57.50 |
| 9 | 0.846 | 0.319 | 62.29 |
| 11 | 1.380 | 0.654 | 52.16 |
| 12 | 1.280 | 0.534 | 58.28 |
| 13 | 0.921 | 0.416 | 54.83 |
| 14 | 0.896 | 0.419 | 53.24 |
| 15 | 1.150 | 0.429 | 62.70 |
| 16 | 1.380 | 0.600 | 56.52 |
| 17 | 0.310 | 0.613 | 53.21 |
| 18 | 0.968 | 0.479 | 50.52 |
| 19 | 1.310 | 0.607 | 53.66 |
| 21 | 1.720 | 0.818 | 52.44 |
| 23 | 1.440 | 0.677 | 52.99 |
| 24 | 1.070 | 0.447 | 58.22 |
| AVERAGE | | | 5.40 |
| STANDARD DEVIATION (SAMPLES) | | | 4.00 |
| COEFFICIENT OF VARIANCE | | | 7.23 |

*WORK DONE IN MILLIJOULES

TABLE 4

GROUP B WET FIBERS: EXPERIMENTAL TREATED WITH SODIUM HYDROXIDE RELAXER WITH 1.4% HYSTAR 6075

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 0.804 | 0.388 | 51.74 |
| 27 | 0.749 | 0.352 | 53.00 |
| 28 | 1.170 | 0.611 | 47.78 |
| 29 | 1.340 | 0.633 | 52.76 |
| 32 | 1.020 | 0.430 | 57.84 |
| 34 | 0.792 | 0.319 | 59.72 |
| 36 | 1.440 | 0.746 | 48.19 |
| 37 | 1.180 | 0.566 | 52.03 |
| 38 | 0.996 | 0.462 | 53.61 |
| 39 | 0.680 | 0.285 | 58.09 |
| 40 | 1.130 | 0.499 | 55.84 |
| 41 | 1.430 | 0.598 | 55.18 |
| 42 | 0.974 | 0.452 | 53.59 |
| 43 | 0.973 | 0.477 | 50.98 |
| 44 | 1.140 | 0.550 | 51.75 |
| 46 | 1.720 | 0.845 | 50.87 |
| 48 | 1.360 | 0.572 | 57.94 |
| 49 | 1.020 | 0.426 | 58.01 |
| AVERAGE | | | 54.01 |
| STANDARD DEVIATION (SAMPLES) | | | 3.65 |
| COEFFICIENT OF VARIANCE | | | 6.76 |

*WORK DONE IN MILLIJOULES

Tables 3 and 4 show that Group A fibers have an average F20 Index loss of 55.40% and Group B fibers have an average F20 Index loss of 54.01%. The t-value equal 1.09. The t-value from Standard-t table at 17 degrees of freedom and 90% probability is equal to 1.74. Therefore, Group B wet fibers which are treated with sodium hydroxide relaxer containing 1.4% Hystar 6075 do not show a significant decrease in the tensile strength at 20.0% elongation compared to Group A wet fibers treated with sodium hydroxide relaxer without Hystar 6075.

Example 3

Group A fibers were treated with sodium hydroxide relaxer without Hystar HM (Composition A of Table A) and Group B fibers were treated with sodium hydroxide relaxer containing 1.5% Hystar HM 75 (Composition D of Table A). The results are shown in Tables 5 and 6.

TABLE 5

GROUP A WET FIBERS: CONTROL TREATED WITH SODIUM HYDROXIDE RELAXER WITHOUT HYSTAR HM

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 2 | 1.640 | 0.949 | 42.13 |
| 4 | 1.200 | 0.572 | 52.33 |
| 5 | 1.270 | 0.644 | 49.29 |
| 8 | 1.780 | 0.354 | 54.62 |
| 9 | 1.160 | 0.571 | 50.78 |
| 10 | 0.440 | 0.736 | 48.89 |
| 12 | 1.060 | 0.549 | 48.21 |
| 13 | 1.540 | 0.790 | 48.70 |
| 14 | 0.983 | 0.479 | 51.27 |
| 15 | 0.966 | 0.367 | 62.01 |
| 17 | 1.100 | 0.557 | 49.36 |
| 19 | 1.370 | 0.650 | 52.55 |
| 20 | 1.210 | 0.586 | 51.57 |
| 21 | 1.200 | 0.534 | 55.50 |
| 22 | 1.040 | 0.463 | 55.48 |
| 23 | 1.230 | 0.502 | 59.19 |
| 25 | 1.090 | 0.537 | 50.73 |
| AVERAGE | | | 51.92 |
| STANDARD DEVIATION (SAMPLES) | | | 4.57 |
| COEFFICIENT OF VARIANCE | | | 8.80 |

*WORK DONE IN MILLIJOULES

TABLE 6

GROUP B WET FIBERS: CONTROL TREATED WITH SODIUM HYDROXIDE RELAXER WITH 1.5% HYSTAR HM

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 27 | 1.470 | 0.899 | 38.84 |
| 29 | 1.050 | 0.593 | 43.52 |
| 30 | 1.150 | 0.630 | 45.22 |
| 33 | 1.703 | 0.412 | 41.39 |
| 34 | 1.030 | 0.545 | 47.09 |
| 35 | 1.420 | 0.824 | 41.97 |
| 37 | 0.995 | 0.523 | 47.44 |
| 38 | 0.790 | 0.410 | 48.10 |
| 39 | 0.995 | 0.523 | 47.98 |
| 40 | 0.790 | 0.410 | 48.10 |
| 42 | 1.090 | 0.567 | 47.98 |
| 44 | 1.220 | 0.661 | 45.82 |
| 45 | 1.080 | 0.619 | 42.69 |
| 46 | 1.040 | 0.533 | 48.75 |
| 47 | 1.080 | 0.578 | 46.48 |
| 48 | 1.270 | 0.642 | 49.45 |
| 50 | 1.040 | 0.571 | 45.10 |
| AVERAGE | | | 45.24 |
| STANDARD DEVIATION (SAMPLES) | | | 2.94 |
| COEFFICIENT OF VARIANCE | | | 6.50 |

*WORK DONE IN MILLIJOULES

Tables 5 and 6 show that Group A fibers have an average F20 Index loss of 51.92% and Group B fibers have an average F20 Index loss of 45.24%. The t-value equals 5.07. The t-value from a Student-t table at 16 degrees of freedom and 95% probability is equal to 2.12. Therefore, Group B wet fibers which are treated with sodium hydroxide relaxer containing 1.5% Hystar HM show significantly less decrease in the tensile strength at 20.0% elongation than Group A wet fibers treated with sodium hydroxide relaxer without Hystar HM75.

Example 4

Group A fibers were treated with sodium hydroxide relaxer without Hystar 7000 (Composition A of Table A) and Group B fibers were treated with sodium hydroxide relaxer containing 1.5% Hystar 7000 (Composition E of Table A). The results are shown in Tables 7 and 8.

TABLE 7

GROUP A WET FIBERS: CONTROL TREATED WITH SODIUM HYDROXDE RELAXER WITHOUT HYSTAR 7000

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | .929 | 0.408 | 56.08 |
| 2 | 1.530 | 0.711 | 53.53 |
| 4 | 1.350 | 0.643 | 52.37 |
| 5 | 1.050 | 0.540 | 48.57 |
| 12 | 1.140 | 0.488 | 57.19 |
| 13 | 1.190 | 0.550 | 53.78 |
| 14 | 1.330 | 0.628 | 52.78 |
| 16 | 1.240 | 0.566 | 54.35 |
| 17 | 1.000 | 0.446 | 55.40 |
| 19 | 1.340 | 0.675 | 49.63 |
| 22 | 0.984 | 0.478 | 51.42 |
| 24 | 1.440 | 0.742 | 48.47 |
| 25 | 1.170 | 0.628 | 46.32 |
| AVERAGE | | | 52.30 |
| STANDARD DEVIATION (SAMPLES) | | | 3.27 |
| COEFFICIENT OF VARIANCE | | | 6.25 |

*WORK DONE IN MILLIJOULES

TABLE 8

GROUP B WET FIBERS: EXPERIMENTAL TREATED WITH SODIUM HYDROXIDE RELAXER WITH 1.5% HYSTAR 7000

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 0.841 | 0.421 | 49.94 |
| 27 | 1.470 | 0.833 | 43.33 |
| 29 | 1.290 | 0.721 | 44.11 |
| 30 | 1.030 | 0.508 | 50.68 |
| 37 | 1.180 | 0.588 | 50.17 |
| 38 | 1.220 | 0.643 | 47.30 |
| 39 | 1.370 | 0.748 | 45.40 |
| 41 | 1.420 | 0.705 | 50.35 |
| 42 | 1.120 | 0.594 | 46.96 |
| 44 | 1.410 | 0.743 | 47.30 |
| 47 | 0.895 | 0.463 | 48.27 |
| 49 | 1.390 | 0.775 | 44.24 |
| 50 | 1.090 | 0.581 | 46.70 |
| AVERAGE | | | 47.29 |
| STANDARD DEVIATION (SAMPLES) | | | 2.52 |
| COEFFICIENT OF VARIANCE | | | 5.33 |

*WORK DONE IN MILLIJOULES

Tables 7 and 8 show that Group A fibers have an average F20 Index loss of 52.30% and Group B fibers have an average F20 Index loss of 47.29%. The t-value equals 4.38. The t-value from a Student-t table at 12 degrees of freedom and 95% probability is equal to 2.18. Therefore, Group B wet fibers which are treated with sodium hydroxide relaxer containing 1.5% Hystar 7000 show significantly less decrease in the tensile strength at 20.0% elongation than Group A wet fibers treated with sodium hydroxide relaxer without Hystar 7000.

Example 5

Group A fibers were treated with sodium hydroxide relaxer without sucrose (Composition A of Table A) and Group B fibers were treated with sodium hydroxide relaxer containing 1.05% sucrose (Composition F of Table A). The results are shown in Tables 9 and 10.

TABLE 9

GROUP A WET FIBERS: CONTROL TREATED WITH SODIUM HYDROXIDE RELAXER WITHOUT SUCROSE

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 1.170 | 0.586 | 49.91 |
| 2 | 0.921 | 0.494 | 46.36 |
| 3 | 1.180 | 0.521 | 56.61 |
| 4 | 0.893 | 0.425 | 52.41 |
| 5 | 0.945 | 0.414 | 56.19 |
| 8 | 1.250 | 0.616 | 50.72 |
| 9 | 1.390 | 0.563 | 59.50 |
| 10 | 1.020 | 0.495 | 51.47 |
| 11 | 1.350 | 0.709 | 47.48 |
| 12 | 1.090 | 0.489 | 55.14 |
| 13 | 0.826 | 0.349 | 57.75 |
| 14 | 0.917 | 0.378 | 58.78 |
| 15 | 0.967 | 0.502 | 48.09 |
| 18 | 1.060 | 0.532 | 49.81 |
| 20 | 0.995 | 0.492 | 50.55 |
| 21 | 0.997 | 0.408 | 59.08 |
| 22 | 0.858 | 0.459 | 46.50 |
| 24 | 0.932 | 0.495 | 46.89 |
| 25 | 0.300 | 0.488 | 62.46 |
| AVERAGE | | | 52.93 |
| STANDARD DEVIATION (SAMPLES) | | | 5.08 |
| COEFFICIENT OF VARIANCE | | | 9.59 |

*WORK DONE IN MILLIJOULES

TABLE 10

GROUP B WET FIBERS: EXPERIMENTAL TREATED WITH SODIUM HYDROXIDE RELAXER WITH 1.05% SUCROSE

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 1.140 | 0.539 | 52.72 |
| 27 | 0.816 | 0.409 | 49.88 |
| 28 | 1.150 | 0.505 | 56.09 |
| 29 | 1.010 | 0.495 | 50.99 |
| 30 | 0.980 | 0.458 | 53.27 |
| 33 | 1.100 | 0.538 | 51.09 |
| 34 | 1.500 | 0.589 | 60.73 |
| 35 | 1.210 | 0.607 | 49.83 |
| 36 | 1.280 | 0.690 | 46.09 |
| 37 | 0.956 | 0.483 | 49.48 |
| 38 | 0.913 | 0.390 | 57.28 |
| 39 | 0.790 | 0.324 | 58.99 |
| 40 | 1.120 | 0.517 | 53.84 |

TABLE 10-continued

GROUP B WET FIBERS: EXPERIMENTAL TREATED WITH SODIUM HYDROXIDE RELAXER WITH 1.05% SUCROSE

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 43 | 0.986 | 0.488 | 50.51 |
| 45 | 0.828 | 0.450 | 45.65 |
| 46 | 0.891 | 0.393 | 55.89 |
| 47 | 0.816 | 0.443 | 45.71 |
| 49 | 0.895 | 0.465 | 48.04 |
| 50 | 1.330 | 0.596 | 55.19 |
| AVERAGE | | | 52.17 |
| STANDARD DEVIATION (SAMPLES) | | | 4.41 |
| COEFFICIENT OF VARIANCE | | | 8.45 |

*WORK DONE IN MILLIJOULES

Tables 9 and 10 show that Group A fibers have an average F20 Index loss of 52.93% and Group B fibers have an average F20 Index loss of 52.17%. The t-value equals 0.489. The t-value from a Student-t table at 18 degrees of freedom and 95% probability is equal to 2.10. Therefore, Group B wet fibers which are treated with sodium hydroxide relaxer containing 1.05% sucrose do not show significantly less decrease in the tensile strength at 20.0% elongation than Group A wet fibers treated with sodium hydroxide relaxer without sucrose.

Example 6

Group A fibers were treated with guanidine relaxer without Hystar CG (Composition A of Table B) and Group B fibers were treated with guanidine relaxer containing 1.5% Hystar CG (Composition B of Table B). The results are shown in Tables 11 and 12.

TABLE 11

GROUP A WET FIBERS: CONTROL TREATED WITH GUANIDINE RELAXER WITHOUT HYSTAR CG

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 1.010 | 0.421 | 58.32 |
| 6 | 1.240 | 0.512 | 58.71 |
| 7 | 1.080 | 0.458 | 57.59 |
| 8 | 1.140 | 0.512 | 55.09 |
| 9 | 1.240 | 0.535 | 56.85 |
| 10 | 1.440 | 0.634 | 55.97 |
| 11 | 1.220 | 0.597 | 51.07 |
| 16 | 1.120 | 0.535 | 52.23 |
| 20 | 1.050 | 0.497 | 52.67 |
| 21 | 0.885 | 0.457 | 48.36 |
| 22 | 0.977 | 0.508 | 48.00 |
| 24 | 1.060 | 0.564 | 46.79 |
| 25 | 1.220 | 0.654 | 46.39 |
| AVERAGE | | | 52.93 |
| STANDARD DEVIATION (SAMPLES) | | | 4.50 |
| COEFFICIENT OF VARIANCE | | | 8.50 |

*WORK DONE IN MILLIJOULES

TABLE 12

GROUP B WET FIBERS: CONTROL TREATED WITH GUANIDINE RELAXER WITH 1.5% HYSTAR CG

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 1.040 | 0.865 | 16.83 |
| 31 | 1.360 | 1.100 | 19.12 |
| 32 | 1.090 | 0.898 | 17.61 |
| 33 | 1.040 | 0.844 | 18.85 |
| 34 | 1.060 | 0.868 | 18.11 |
| 35 | 1.560 | 1.270 | 18.59 |
| 36 | 1.250 | 1.030 | 17.60 |
| 41 | 1.210 | 0.951 | 21.40 |
| 45 | 0.933 | 0.746 | 20.04 |
| 46 | 0.954 | 0.783 | 17.92 |
| 47 | 0.889 | 0.717 | 19.35 |
| 49 | 1.030 | 0.806 | 21.75 |
| 50 | 1.130 | 0.948 | 16.11 |
| AVERAGE | | | 18.71 |
| STANDARD DEVIATION (SAMPLES) | | | 1.65 |
| COEFFICIENT OF VARIANCE | | | 8.81 |

*WORK DONE IN MILLIJOULES

Tables 11 and 12 show that Group A fibers have an average F20 Index loss of 52.93% and Group B fibers have an average F20 Index loss of 18.71%. The t-value equals 25.74. The t-value from Table T at 12 degrees of freedom and 95% probability is equal to 2.18. Therefore, Group B wet fibers which are treated with guanidine relaxer containing 1.5% Hystar CG show significantly less decrease in the tensile strength at 20.0% elongation than Group A wet fibers treated with guanidine relaxer without Hystar CG.

Example 7

Group A fibers were treated with guanidine relaxer without Hystar 6075 (Composition A of Table B) and Group B fibers were treated with guanidine relaxer containing 1.4% Hystar 6075 (Composition C of Table B). The results are shown in Tables 13 and 14.

TABLE 13

GROUP A WET FIBERS: CONTROL TREATED WITH GUANIDINE RELAXER WITHOUT HYSTAR 6075

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 1.110 | 0.450 | 59.46 |
| 4 | 1.160 | 0.414 | 64.31 |
| 5 | 1.610 | 0.596 | 62.98 |
| 8 | 1.310 | 0.601 | 54.12 |
| 15 | 0.944 | 0.422 | 55.30 |
| 17 | 0.945 | 0.370 | 60.85 |
| 22 | 1.170 | 0.564 | 51.79 |
| 23 | 1.250 | 0.476 | 61.92 |
| AVERAGE | | | 58.84 |
| STANDARD DEVIATION (SAMPLES) | | | 4.56 |
| COEFFICIENT OF VARIANCE | | | 7.75 |

*WORK DONE IN MILLIJOULES

TABLE 14

GROUP B WET FIBERS: CONTROL TREATED WITH GUANIDINE RELAXER WITH 1.4% HYSTAR 6075

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 1.100 | 0.863 | 21.55 |
| 29 | 1.020 | 0.812 | 20.39 |
| 30 | 1.450 | 1.160 | 20.00 |
| 33 | 1.390 | 1.170 | 15.83 |
| 40 | 1.010 | 0.848 | 16.04 |
| 42 | 0.855 | 0.665 | 22.22 |
| 47 | 1.300 | 1.050 | 19.23 |
| 48 | 1.250 | 1.000 | 20.00 |
| AVERAGE | | | 19.41 |
| STANDARD DEVIATION (SAMPLES) | | | 2.34 |
| COEFFICIENT OF VARIANCE | | | 12.06 |

*WORK DONE IN MILLIJOULES

Tables 13 and 14 show that Group A fibers have an average F20 Index loss of 58.84% and Group B fibers have an average F20 Index loss of 19.41%. The t-value equals 21.78. The t-value from a Standard-t table at 7 degrees of freedom and 95% probability is equal to 2.37. Therefore, Group B wet fibers which are treated with guanidine relaxer containing 1.4% Hystar 6075 show significantly less decrease in the tensile strength at 20.0% elongation than Group A wet fibers treated with guanidine relaxer without Hystar 6075.

Example 8

Group A fibers were treated with guanidine relaxer without Hystar 7000 (Composition A of Table B) and Group B fibers were treated with guanidine relaxer containing 1.5% Hystar 7000 (Composition D of Table B). The results are shown in Tables 15 and 16.

TABLE 15

GROUP A WET FIBERS: CONTROL TREATED WITH GUANIDINE RELAXER WITHOUT HYSTAR 7000

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 1.360 | 0.790 | 41.91 |
| 2 | 1.460 | 0.813 | 44.32 |
| 3 | 1.070 | 0.533 | 50.19 |
| 7 | 1.320 | 0.726 | 45.00 |
| 8 | 1.010 | 0.553 | 45.25 |
| 9 | 1.350 | 0.776 | 42.52 |
| 10 | 1.560 | 0.853 | 45.32 |
| 13 | 0.959 | 0.489 | 49.01 |
| 14 | 0.969 | 0.523 | 46.03 |
| 17 | 0.919 | 0.487 | 47.01 |
| 20 | 1.760 | 0.920 | 47.73 |
| 22 | 1.280 | 0.780 | 39.06 |
| 23 | 1.080 | 0.545 | 49.54 |
| AVERAGE | | | 45.61 |
| STANDARD DEVIATION (SAMPLES) | | | 3.20 |
| COEFFICIENT OF VARIANCE | | | 7.02 |

*WORK DONE IN MILLIJOULES

TABLE 16

GROUP B WET FIBERS: EXPERIMENTAL TREATED WITH GUANIDINE RELAXER WITH 1.5% HYSTAR 7000

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 1.230 | 0.998 | 18.86 |
| 27 | 1.350 | 1.120 | 17.04 |
| 28 | 1.010 | 0.809 | 19.90 |
| 32 | 1.350 | 1.090 | 19.26 |
| 33 | 0.874 | 0.678 | 22.43 |
| 34 | 1.410 | 1.100 | 21.99 |
| 35 | 1.530 | 1.240 | 18.95 |
| 38 | 1.060 | 0.893 | 15.75 |
| 39 | 1.010 | 0.812 | 19.60 |
| 42 | 0.939 | 0.749 | 20.23 |
| 45 | 1.390 | 1.160 | 16.55 |
| 47 | 1.320 | 1.080 | 18.18 |
| 48 | 0.982 | 0.790 | 19.55 |
| AVERAGE | | | 19.10 |
| STANDARD DEVIATION (SAMPLES) | | | 1.93 |
| COEFFICIENT OF VARIANCE | | | 10.10 |

*WORK DONE IN MILLIJOULES

Tables 15 and 16 show that Group A fibers have an average F20 Index loss of 45.61% and Group B fibers have an average F20 Index loss of 19.10%. The t-value equals 25.58. The t-value from a Standard-t table at 12 degrees of freedom and 95% probability is equal to 2.18. Therefore, Group B wet fibers which are treated with guanidine relaxer containing 1.4% Hystar 7000 show significantly less decrease in the tensile strength at 20.0% elongation than Group A wet fibers treated with guanidine relaxer without Hystar 7000.

Example 9

Group A fibers were treated with guanidine relaxer without HM 75 (Composition A of Table B) and Group B fibers were treated with guanidine relaxer containing 1.5% HM 75 (Composition E of Table B). The results are shown in Tables 17 and 18.

TABLE 17

GROUP A WET FIBERS: CONTROL TREATED WITH GUANIDINE RELAXER WITHOUT HYSTAR HM 75

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 7 | 1.390 | 0.607 | 56.33 |
| 8 | 1.070 | 0.466 | 56.45 |
| 9 | 1.330 | 0.641 | 51.80 |
| 10 | 1.290 | 0.560 | 56.59 |
| 11 | 1.140 | 0.461 | 59.56 |
| 13 | 1.140 | 0.515 | 54.82 |
| 14 | 0.986 | 0.426 | 56.80 |
| 15 | 1.360 | 0.618 | 54.56 |
| 16 | 0.998 | 0.370 | 62.93 |
| 17 | 0.912 | 0.434 | 52.41 |
| 18 | 1.690 | 0.675 | 60.06 |
| 22 | 1.120 | 0.537 | 52.05 |
| 23 | 1.000 | 0.466 | 53.40 |
| 24 | 1.150 | 0.521 | 54.70 |
| 25 | 1.520 | 0.731 | 51.91 |
| AVERAGE | | | 55.62 |
| STANDARD DEVIATION (SAMPLES) | | | 3.28 |
| COEFFICIENT OF VARIANCE | | | 5.90 |

*WORK DONE IN MILLIJOULES

TABLE 18

GROUP B WET FIBERS: EXPERIMENTAL TREATED WITH GUANIDINE RELAXER WITH 1.5% HYSTAR HM 75

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 32 | 1.280 | 0.981 | 23.36 |
| 33 | 0.929 | 0.688 | 25.94 |
| 34 | 1.250 | 0.995 | 20.40 |
| 35 | 1.250 | 0.995 | 20.40 |
| 36 | 1.060 | 0.807 | 23.87 |
| 38 | 1.120 | 0.889 | 20.63 |
| 39 | 0.951 | 0.720 | 24.29 |
| 40 | 1.360 | 1.060 | 22.06 |
| 41 | 1.360 | 1.060 | 22.06 |
| 42 | 0.841 | 0.666 | 20.81 |
| 43 | 1.490 | 1.130 | 24.16 |
| 47 | 1.200 | 0.913 | 23.92 |
| 48 | 0.935 | 0.723 | 22.67 |
| 49 | 1.250 | 1.010 | 19.20 |
| 50 | 1.250 | 1.010 | 19.20 |
| AVERAGE | | | 22.20 |
| STANDARD DEVIATION (SAMPLES) | | | 2.04 |
| COEFFICIENT OF VARIANCE | | | 9.21 |

*WORK DONE IN MILLIJOULES

Tables 17 and 18 show that Group A fibers have an average F20 Index loss of 55.62% and Group B fibers have an average F20 Index loss of 22.20%. The t-value equals 33.51. The t-value from a Standard-t table at 14 degrees of freedom and 95% probability is equal to 2.15. Therefore, Group B wet fibers which are treated with guanidine relaxer containing 1.5% Hystar 75 show significantly less decrease in the tensile strength at 20.0% elongation than Group A wet fibers treated with guanidine relaxer without Hystar HM 75.

Example 10

Group A fibers were treated with guanidine relaxer without sucrose (Composition A of Table B) and Group B fibers were treated with guanidine relaxer containing 1.05% sucrose (Composition F of Table B). The results are shown in Tables 19 and 20.

TABLE 19

GROUP A WET FIBERS: CONTROL TREATED WITH GUANIDINE RELAXER WITHOUT SUGAR

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 1 | 1.080 | 0.539 | 50.09 |
| 3 | 1.090 | 0.535 | 50.92 |
| 4 | 1.130 | 0.530 | 53.10 |
| 5 | 1.320 | 0.583 | 55.83 |
| 7 | 0.943 | 0.444 | 52.92 |
| 9 | 0.935 | 0.431 | 53.90 |
| 11 | 0.950 | 0.435 | 54.21 |
| 13 | 1.320 | 0.649 | 50.83 |
| 15 | 1.300 | 0.597 | 54.08 |
| 17 | 1.160 | 0.575 | 50.43 |
| 18 | 0.987 | 0.456 | 53.80 |
| 20 | 1.410 | 0.684 | 51.49 |
| 21 | 1.310 | 0.632 | 51.76 |
| 22 | 1.050 | 0.419 | 60.10 |
| 23 | 1.020 | 0.442 | 56.67 |
| 24 | 1.020 | 0.443 | 56.57 |
| AVERAGE | | | 53.54 |
| STANDARD DEVIATION (SAMPLES) | | | 2.73 |
| COEFFICIENT OF VARIANCE | | | 5.10 |

*WORK DONE IN MILLIJOULES

TABLE 20

GROUP B WET FIBERS: EXPERIMENTAL TREATED WITH GUANIDINE RELAXER WITH 1.05% SUGAR

| FIBER NO. | INITIAL WORK DONE* X | WORK DONE* AFTER RELAXER Y | F20 INDEX AFTER RELAXER TREATMENT (% Loss in Tensile Strength) |
|---|---|---|---|
| 26 | 1.240 | 0.948 | 23.55 |
| 28 | 1.220 | 0.943 | 22.70 |
| 29 | 0.998 | 0.805 | 19.34 |
| 30 | 1.260 | 0.989 | 21.51 |
| 32 | 0.892 | 0.674 | 24.44 |
| 34 | 0.859 | 0.663 | 22.82 |
| 36 | 0.898 | 0.696 | 22.49 |
| 38 | 1.380 | 1.080 | 21.74 |
| 40 | 1.300 | 1.030 | 20.77 |
| 42 | 1.300 | 1.010 | 22.31 |
| 43 | 1.080 | 0.855 | 20.83 |
| 45 | 1.330 | 1.070 | 19.55 |
| 46 | 1.450 | 1.190 | 17.93 |
| 47 | 1.110 | 0.866 | 21.98 |
| 48 | 1.180 | 0.918 | 22.20 |
| 49 | 0.921 | 0.727 | 21.06 |
| AVERAGE | | | 21.58 |
| STANDARD DEVIATION (SAMPLES) | | | 1.65 |
| COEFFICIENT OF VARIANCE | | | 7.64 |

*WORK DONE IN MILLIJOULES

Tables 19 and 20 show that Group A fibers have an average F20 Index loss of 53.54% and Group B fibers have an average F20 Index loss of 21.58%. The t-value equals 40.08. The t-value from a Standard-t table at 15 degrees of freedom and 95% probability is equal to 2.13. Therefore, Group B wet fibers which are treated with guanidine relaxer containing 1.05% sucrose show significantly less decrease in the tensile strength at 20.0% elongation than Group A wet fibers treated with guanidine relaxer without sucrose.

What is claimed is:

1. A process for reducing damage to hair during lanthionizing, comprising the steps of:

a. applying to hair fibers a lanthionizing composition consisting essentially of a lanthionizing agent of p.H. in a range of 12.0 to 13.5, a hydrogenated starch hydrolysate and/or a sugar;

b. allowing the lanthionizing composition to remain on the hair fibers for a time sufficient to obtain the desired degree of lanthionization; and c. removing the lanthionizing composition from the hair fibers.

2. The process according to claim 1 wherein the sugar is sucrose, glucose, fructose or glycerol.

3. The process according to claim 2 wherein the sugar is sucrose.

4. The process according to claim 1 wherein the sugar is found in the lanthionizing composition in an amount in the range of about 0.1% to about 5.0% by weight of the lanthionizing composition.

5. The process according to claim 1 wherein the sugar is found in the lanthionizing composition in an amount in the range of about 0.31% to about 5.0% by weight of the lanthionizing compound.

6. The process according to claim 1 wherein the hydrogenated starch hydrolysate is found in the lanthionizing composition in an amount in the range of about 0.1% to about 5.0% by weight of the lanthionizing composition.

7. The process according to claim 1 wherein the hydrogenated starch hydrolysate is found in the lanthionizing composition in an amount in the range of about 0.25% to about 1.5% by weight of the lanthionizing composition.

8. A lanthionizing composition consisting essentially of a lanthionizing agent, a hydrogenated starch hydrolysate and/or a sugar.

9. The composition of claim 8 wherein the sugar is sucrose, glucose, fructose, or glycerol.

10. The composition of claim 9 wherein the sugar is sucrose.

11. The composition according to claim 8 wherein the sugar is found in the lanthionizing composition in an amount in the range of about 0.1% to about 5.0% by weight of the lanthionizing composition.

12. The composition according to claim 8 wherein the sugar is found in the lanthionizing composition in the range of about 0.31% to about 1.5% by weight of the lanthionizing composition.

13. The composition according to claim 8 wherein the hydrogenated starch hydrolysate is found in the lanthionizing composition in an amount in the range of about 0.1% to about 5.0% by weight of the lanthionizing composition.

14. A process for reducing damage to hair during lanthionizing, the process comprising the steps of:

a. applying to hair fibers a lanthionizing composition consisting essentially of a lanthionizing agent of p.H. in a range of 12.0 to 13.5 and sucrose in an amount in the range of about 0.31% to about 1.5% by weight of the lanthionizing composition;

b. allowing the lanthionizing composition to remain on the hair fibers for a time sufficient to obtain the desired degree of lanthionization; and c. removing the lanthionization composition from the hair fibers.

15. A process for reducing damage to hair during lanthionizing, the process comprising the steps of:

a. applying to hair fibers a lanthionizing composition consisting essentially of a lanthionizing agent of p.H. in a range of 12.0 to 13.5 and a hydrogenated starch hydrolysate in an amount in the range of about 0.25% to about 1.5% by weight of the lanthionizing composition;

b. allowing the lanthionizing composition to remain on the hair fibers for a time sufficient to obtain the desired degree of lanthionization; and c. removing the lanthionization composition from the hair fibers.

16. The lanthionizing composition according to claim 8 that comprises a sugar in an amount in the range of about 0.31% to about 1.5% by weight of the lanthionizing composition.

17. The composition of claim 16 wherein the sugar is glucose, fructose or glycerol.

18. The lanthionizing composition according to claim 8 that comprises a hydrogenated starch hydrolysate in an amount in the range of about 0.25% to about 1.5% by weight of the lanthionizing composition.

* * * * *

UNITED STATES PATENT AND TRADEMARK OFFICE
CERTIFICATE OF CORRECTION

PATENT NO. : 5,641,477
DATED : 24 June 1997
INVENTOR(S) : Syed et al.

It is certified that error appears in the above-identified patent and that said Letters Patent is hereby corrected as shown below:

In Column 1, line 47, please delete "a so" and insert "also"
In Column 5, line 10, please delete "min." and insert "mm."
In Column 6, lines 55 and 56, please delete "avenge" and insert "average"
In Column 7, line 15, please delete " $Sd=\sqrt{Sd^2}$ " and insert " $Sd=\sqrt{Sd^2}$ "
In Column 7, line 25, insert a line for space between paragraphs Signed and Sealed this Sixth Day of January, 1998

Attest:

BRUCE LEHMAN

Attesting Officer

Commissioner of Patents and Trademarks